United States Patent
Honkura et al.

(10) Patent No.: US 6,299,450 B1
(45) Date of Patent: *Oct. 9, 2001

(54) DENTAL MAGNETIC ATTACHMENT

(75) Inventors: Yoshinobu Honkura, Higashiura-cho; Kazuo Arai, Tokai; Kazunari Kimura, Chita; Lei Tian, Tokai, all of (JP)

(73) Assignee: Aichi Steel Corporation, Tokai (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/427,702

(22) Filed: Oct. 27, 1999

(30) Foreign Application Priority Data

Apr. 23, 1998 (JP) .................................................. 10-113368
Oct. 20, 1999 (JP) .................................................. 11-297785

(51) Int. Cl.⁷ .................................................. A61C 13/235
(52) U.S. Cl. .......................................... 433/189; 335/302
(58) Field of Search .............................. 433/189; 335/302

(56) References Cited

U.S. PATENT DOCUMENTS

| 4,626,213 | * | 12/1986 | Shiner et al. | 433/189 |
| 4,815,975 | * | 3/1989 | Garrel et al. | 433/189 |
| 5,013,243 | * | 5/1991 | Tanaka et al. | 433/189 |
| 5,337,033 |   | 8/1994 | Kinouchi et al. | 433/189 |
| 5,788,493 |   | 8/1998 | Tanaka et al. | 433/189 |

FOREIGN PATENT DOCUMENTS

| 4-227253 | 8/1992 | (JP) . |
| 5-68688 | 3/1993 | (JP) . |
| 6-169937 | 6/1994 | (JP) . |
| 6-86713 | 12/1994 | (JP) . |
| 6-86714 | 12/1994 | (JP) . |
| 6-86715 | 12/1994 | (JP) . |

OTHER PUBLICATIONS

Development of Sealed Cup Yoke Type Dental Magnetic Attachment Dental Materials Journal, vol. 10, No. 2, 172–184, Dec., 1991.
Improvements of the Cup Yoke Magnetic Attachment by Use of a Thinner Shield Ring, Jan., 1993, Okuno et al.

* cited by examiner

Primary Examiner—John J. Wilson
(74) Attorney, Agent, or Firm—Jacobson Holman, PLLC

(57) ABSTRACT

A dental magnetic attachment which has a superior magnetic attractive force with a small nonmagnetic welded part and a flat welded surface to be polished. The dental magnetic attachment including a magnet, a yoke with a pit to hold the magnet, a sealing disk placed on the opening of the pit to cover the magnet and a nonmagnetic welded part between the yoke and the disk. The yoke and the disk are made from soft magnetic material. The nonmagnetic welded part, which joins the yoke and the disk, is formed by welding the yoke, the sealing disk, the sealing ring made from nonmagnetic austenitic stainless steel and a Ni coat between the sealing disk and the sealing ring together. Here, it is preferably that there remains a part of the nonmagnetic sealing ring. The welded surface of the dental magnetic attachment is polished to be flat.

3 Claims, 6 Drawing Sheets

DENTAL MAGNETIC ATTACHMENT

BACKGROUND OF THE INVENTION

1. Field of the Invention

The present invention relates to a thin-type dental magnetic attachment which is embedded in a pit of a denture to hold the denture on teeth roots in the oral cavity using magnetic attractive force.

2. Description of the Related Art

Presently, a dental magnetic attachment which strongly holds and stabilizes the denture on teeth roots by magnetic attractive force is well known. As shown in FIG. 8, its force acts between a dental magnetic attachment 9 in a denture 80 and a keeper 10 made from a soft magnetic material embedded in a root cap 85 inserted into a tooth root 86. The denture 80 has artificial teeth 84, a resin base 83 and a dental magnetic attachment 9. Japanese Patent application Laid open (Kokai) No. 4-227253 discloses a round shaped dental magnetic attachment shown in FIG. 9.

This dental magnetic attachment 9 is composed from a cylindrical shaped magnet 91, a cylindrical shaped yoke 92 having a pit 99 for holding the magnet, and a sealing plate 98 for covering the bottom of the magnet. Here the sealing plate consists of a sealing disk 96 and a sealing ring 97. The yoke, the sealing disk and the keeper are made from soft magnetic materials. The magnet is magnetized to the normal direction to the magnetic attached plane between the dental magnetic attachment and the keeper. When the dental magnetic attachment is set on the keeper, a closed magnetic circuit composed from the magnet, the yoke and keeper is formed. The magnetic flux flows from the top of the magnet, through the yoke, the keeper and the sealing disk back to the bottom of the magnet. The sealing ring made from nonmagnetic material is placed between the yoke and the sealing disk to prevent occurrence of a magnetic short circuit. All of the parts except the magnet are made from corrosion resistant materials.

The sealing disk 96 and the sealing ring 97 are joined to the yoke by laser welding. The laser welding lines are two boundaries between the yoke and the outer side of the sealing ring and between the sealing disk and the inner side of the sealing ring. That means that laser welding is done two times.

However the above invention has some serious disadvantages concerning the sealing method. In the case that the sealing ring has a comparatively large width, the laser welding can be done easily, but the area of the disk becomes so small that the magnetic attractive force decreases. On the other hand, in the case that the sealing ring is narrow, it is very difficult to laser-weld the sealing ring to both the yoke and the sealing disk. Large strain or stress produced by the heat in welding is apt to make some gap or step among the sealing ring, the yoke and the sealing disk. Sometimes cracks occur in the welded parts.

To solve the above disadvantages, another sealing method as shown in FIG. 10 is proposed in the proceedings of the annual meeting of the Japanese Metal Society, at p408 (1996). This dental magnetic attachment is produced by a laser-welding technique of a single application instead of the above laser-welding technique of two times. Its small welded part works as a nonmagnetic sealing ring to contribute an increase in the magnetic attractive force.

In this method, a sealing disk 106 is plated or coated by Ni. It means that Ni coat 105 which is a soft magnetic material is substituted for the nonmagnetic sealing ring. The Ni coated disk is placed on the magnet 101 inserted into the pit 108 of the yoke 102 and then it is laser-welded to the yoke. At this time, Ni coat is melt together with the yoke 102 and the sealing disk 106 made from soft magnetic stainless steel and the nonmagnetic welded part is formed. However this method has some inevitable defects.

It is required that the depth of the welded part is controlled to be just equal to the thickness of the sealing disk. If the depth is not enough as shown by a dotted line (F) in FIG. 10(B) and Ni coat remains, a magnetic short circuit is formed because Ni metal is of soft magnetic materials. Consequently, the magnetic attractive force decreases remarkably. If the depth is too large as shown by a dotted line (E) shown in FIG. 10(B), the heat of laser-welding process damages the magnet so as to cause a decrease of the magnetic attractive force. When a magnet with a small diameter is applied, the magnet is free from this damage, but it is natural that the magnetic attractive force becomes small.

Moreover, the welded part is apt to become an imperfect austenite phase to contain a small volume of ferrite phase. This means that it is difficult to make the welded part nonmagnetic. The reason of the occurrence of the ferrite phase is considered with the Schaeffler diagram which gives the phase constitution after welding stainless steels. A soft magnetic stainless steel of SUS447J1 type with 30% Cr, 2% Mo and residual of iron is used as the yoke material in the above paper. The welded part shows a chemical composition having more than 15% Ni but it has a large part of ferrite phase. This results in a weak magnetic short circuit between the yoke 102 and the sealing disk 106 to make an undesirable decrease in the magnetic attractive force.

If another soft magnetic stainless steel of SUS430 type having 17% Cr and residual of iron is used instead of SUS447J1 type, nonmagnetic welded part would be obtained to give high magnetic attractive force. But the welded part has less than 17% Cr to become very corrosive in the oral cavity.

It is noted that the thickness of the sealing disk is so thin around 0.2 mm, that a laser-welding process with the yoke and the disk is very difficult normally, and yet in the case of the Ni coated sealing disk the laser-welding process is more difficult. Consequently, this dental magnetic attachment has been not yet produced.

SUMMARY OF THE INVENTION

The present invention intends to solve the difficulty of the laser-welding process and offer a dental magnetic attachment with a round shape, which has a strong magnetic attractive force.

A dental magnetic attachment of the present invention is characterized by nonmagnetic welded part between the yoke and the sealing disk.

The basic structure of the present magnetic assembly is similar to ones disclosed by Japanese Patent application Laid open (Kokai) No. 4-227253, but the nonmagnetic welded part is very different. The dental magnetic attachment is composed from a cylindrical shaped magnet, a cylindrical shaped yoke having a pit for holding the magnet, and a sealing plate for covering the bottom of the magnet which plate consists of a sealing disk and a sealing ring. Here the inner surface of the sealing ring is plated or coated by Ni. The yoke, the sealing disk and the keeper are made from soft magnetic material. The sealing ring is made from nonmagnetic stainless steel. The sealing disk and the sealing ring are joined to the yoke by laser welding with only one welding line. The welded part becomes nonmagnetic and keeps the space between the yoke and the sealing disk nonmagnetic to make a magnetic isolation barrier. After being laser-welded, the welded surface is polished to make flat.

The first point of the present invention is that the welded part of the dental magnetic attachment becomes nonmagnetic by melting the sealing ring coated by Ni together with the yoke and the sealing disk. The second is that there is only one welded line. The third is that the corner of the magnet is polished round. And the fourth is that the welded surface is polished to be made flat and the sealing disk is made thinner.

The effects of the present invention are as follows.

The present invention can make the space between the yoke and the sealing disk nonmagnetic certainly by means of the laser welding technique to form a nonmagnetic welded part and can improve the magnetic attractive force. The welded part is formed by melting four parts which are the yoke, the sealing ring, Ni coat and the sealing disk. But the chemical composition of the welded part is near to that of nonmagnetic stainless steel of the sealing ring and the welded part certainly becomes nonmagnetic. The soft magnetic material of the yoke and the disk tends to make the welded part magnetic. The element in the Ni. coat tends to make it nonmagnetic. Two materials are mixed to cancel both effects and to make no or little change in the chemical composition of the welded part from nonmagnetic stainless steel of the sealing ring. The welded part is mainly dependent on the nonmagnetic stainless steel of the sealing ring.

The second point of the present invention is to polish or grind the welded plane. The polishing process makes the disk thinner, reduces the width of the nonmagnetic welded part, enlarges the area of the disk and make the surface flat, which leads to the improvement in the magnetic attractive force. Especially the welded surface has a large inequality. If it is not polished to be flat, the attached surface has some air gap to bring a remarkable decrease in the attractive force. The third is to polish the corners of the magnet to become round. The round corners protect the magnet from the heat of welding to hold the strong attractive force. The fourth point is only one welded line. This means that welding can be done easily, which makes small strain and stress to reduce the deformation, gap and crack in the welded part.

The corrosion resistant soft magnetic materials used for the above sealing disk are stainless steels such as 19% Cr-2% Mo-0.2% Ti steel, 17% Cr-2% Mo-0.2% Ti steel and 13% Cr-2% Mo-0.2% Ti steel. The nonmagnetic materials used for the above sealing ring are stainless steels such as SUS304 type, SUS316 type, SUS316L type and SUS310S type.

A dental magnetic attachment of the present invention is characterized by the nonmagnetic welded part made from austenitic stainless steel to have a perfect austenite phase. It is preferable that the ring shape welded part has a chemical composition which contains austenitic stainless steel to keep nonmagnetic and good corrosion resistance.

FIG. 7 is a Schaffler diagram to show phase constitution of a welded part of stainless steel. When the yoke, the sealing disk and the sealing ring are welded, the soft magnetic stainless steel used for the yoke and the sealing disk, the nonmagnetic stainless steel used for the sealing ring and the Ni element in the Ni coat are melted together and mixed to form a welded metal.

The chemical composition and the phase constitution for welded metal are roughly expected from this Schaffler diagram. In the case that there is no Ni coat, both alloys of the nonmagnetic stainless steel used for the sealing ring and the soft magnetic stainless steel used for the yoke and the sealing disk are mixed. The chemical composition of the welded metal is dependent on the chemical compositions and melted volumes of both alloys. It is sure that the welded metal has far less than Ni content and more than Cr content compared with the nonmagnetic stainless steel used for the sealing ring. As seen from FIG. 7, the welded metal in the welded part show a position in the diagram to stand a large martensite or ferrite phase which are soft magnetic. Without Ni coat, the welded part does not show nonmagnetic.

The Ni element in the Ni coat plays an important role to make the phase constitution of the welded metal nonmagnetic austenite phase. When both alloys of the nonmagnetic stainless steel and the soft magnetic stainless steel and the Ni coat are melted together, the welded metal has enriched Ni content to change from dual phase of austenite and ferrite to single austenite phase.

A dental magnetic attachment of the present invention is characterized by the nonmagnetic welded part which has more than half the thickness of the sealing disk. When the thickness of the welded part is less than that of the sealing disk, the nonmagnetic sealing ring remains. Both the residual ring and the welded part form the nonmagnetic space between the yoke and the sealing disk to form a magnetic isolation. The present dental magnetic attachment offers advantages to maintain magnetic isolation and to protect the magnet from heat damage during welding. In addition, the welded part is small in width and the area of the sealing disk become wider to make certain improvements in the magnetic attractive force of the dental magnetic attachment. But it is noted that when the thickness of the welded part are less than half of the sealing disk, the joint strength of the welded part becomes too weak an will begin to fracture.

A dental magnetic attachment of the present invention is characterized by the nonmagnetic welded part which is polished to be flat and 0.05 mm to 0.15 mm in thickness. The welded surface of the dental magnetic attachment is polished at least 0.05 mm in thickness because the welded part has inequality of more than 0.05 mm. To polish it too much makes the welded part and the sealing disk thinner in thickness to reduce the joint strength and cause fracture in use. As for the thickness of the sealing disk, it is preferable to be less than 0.150 mm because the thick sealing disk reduces the magnetic attractive force and makes the dental magnetic attachment bigger in height.

As for the magnet used in the present invention, it is preferable to use rare earth magnets such as Sm—Co type magnet and Nd—Fe—B type magnet having high maximum energy product and high coercivity. The one corner of the cylindrical magnet at least is polished to be round with a curvature radius of 0.10 mm to 0.30 mm. The curvature radius of more than 0.10 mm is required to protect the magnet from the heat during welding. The curvature radius of more than 0.30 mm is not preferable because it makes the magnet small and brings a certain decrease in the magnetic attractive force.

When both corners of the cylindrical magnet are polished to be round, another merit is achieved. It the bottom corner of the pit of the yoke as well as the magnet is formed to be round, the magnet with a round corner can be inserted without making a gap in the pit. The round bottom corner of the pit of the yoke can make a remarkable increase in the magnetic attractive force of the dental magnetic attachment because of the smooth flow of magnetic flux.

As for the yoke, the shape looks like a container for inserting the magnet. And it is preferable that the yoke is made from soft magnetic and corrosion resistant materials such as 18% Cr stainless steel, 17% Cr-2% Mo stainless steel, 19% Cr-2% Mo stainless steel and so on. The yoke materials are required to have good corrosion resistance in the oral cavity and excellent magnetic properties to make a magnetic circuit.

PREFERRED EMBODIMENT OF THE PRESENT INVENTION

Three kinds of embodiments according to the present invention are described with reference to FIG. 1 to FIG. 7.

Figure 1:
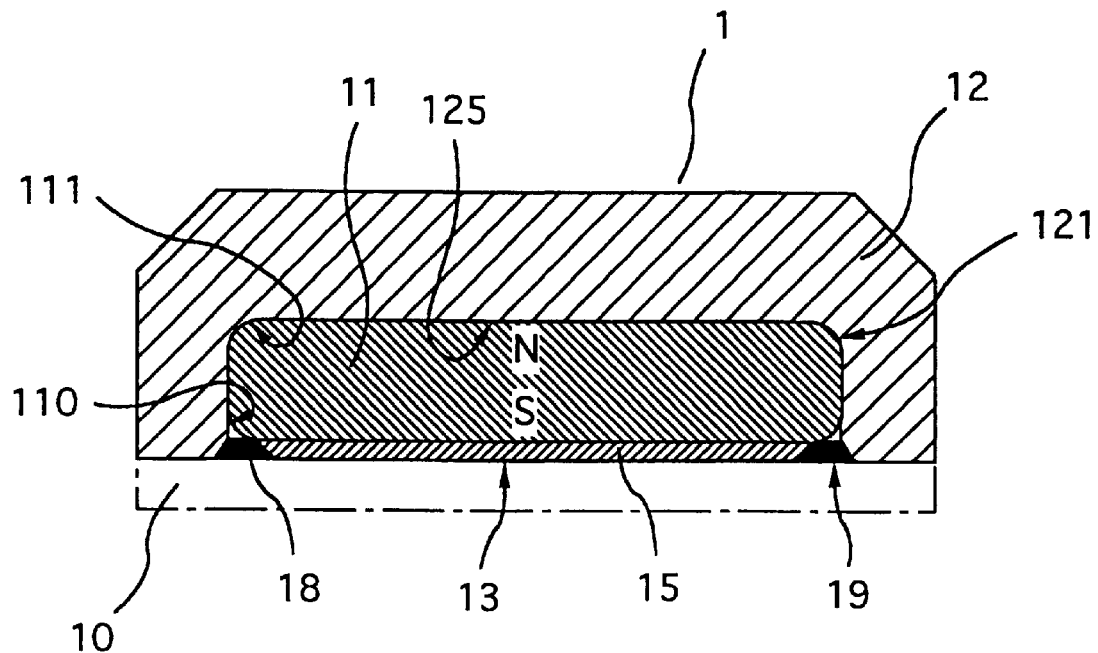
FIG. 1 is a cross section to show the construction of the first example.

The dental magnetic attachment 1 of the first example is shown in FIG. 1. It is comprised of a cylindrical shaped magnet 11, a cylindrical shaped yoke 12 having a pit 125 for holding the magnet, a sealing disk 15 for covering the bottom of the magnet 19 and a nonmagnetic welded part 18 between the yoke and the sealing disk. Here the nonmagnetic welded part is formed to weld the yoke, the sealing ring, Ni coat and the sealing disk together. And the welded surface 13 of the dental magnetic attachment is polished to be flat.

Figure 2:
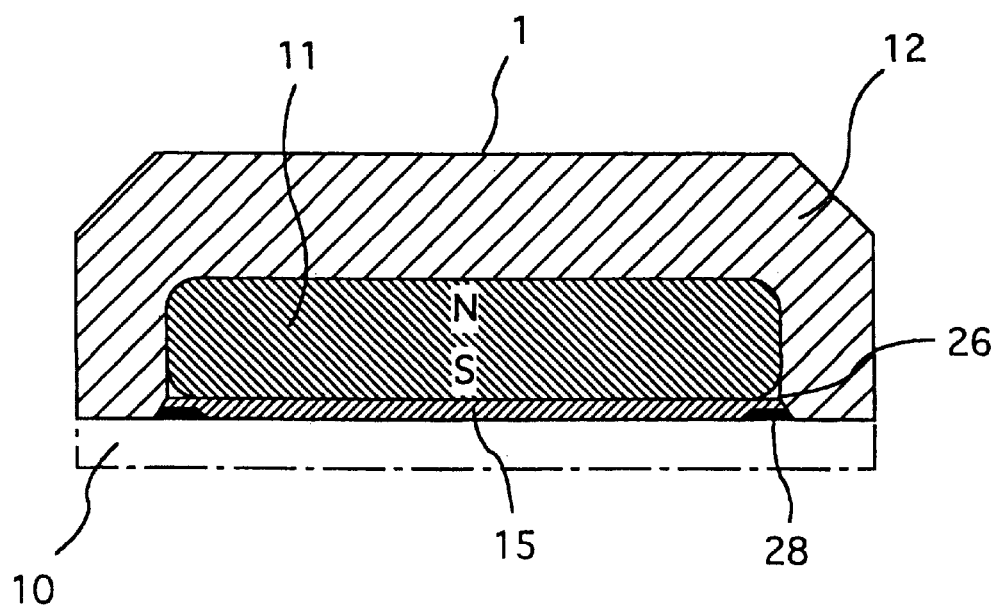
FIG. 2 is a cross section to show the construction of the first example.

The dental magnetic attachment of the second example is similar to the first one as shown in FIG. 2. However, the thickness of the nonmagnetic welded part 28 is thinner than that of the sealing disk 15. There remains a part of the nonmagnetic sealing ring 26. To make provision against mechanical failure, the thickness of the nonmagnetic welded part must keep more than a half of the sealing disk.

Figure 3:
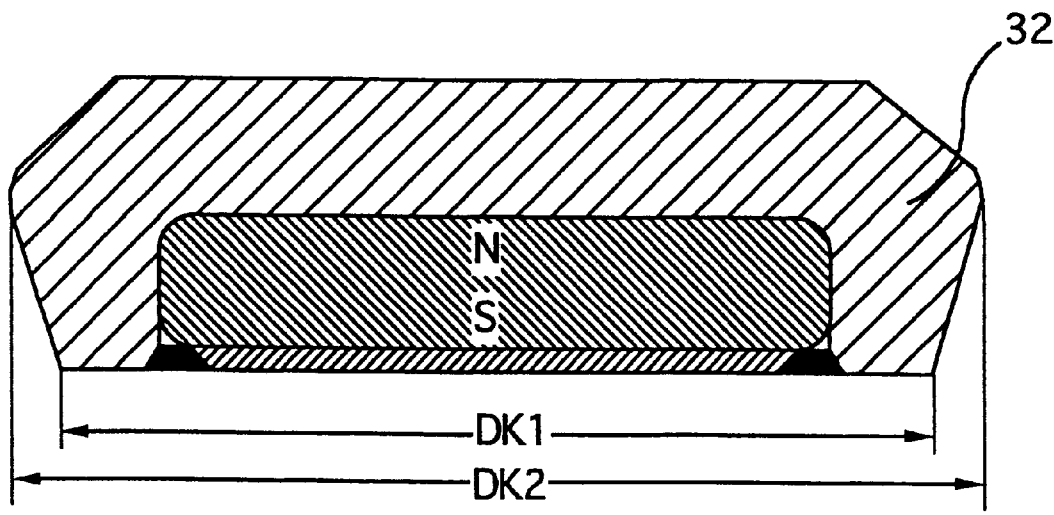
FIG. 3 is a cross section to show the construction of the first example.
Figure 8:
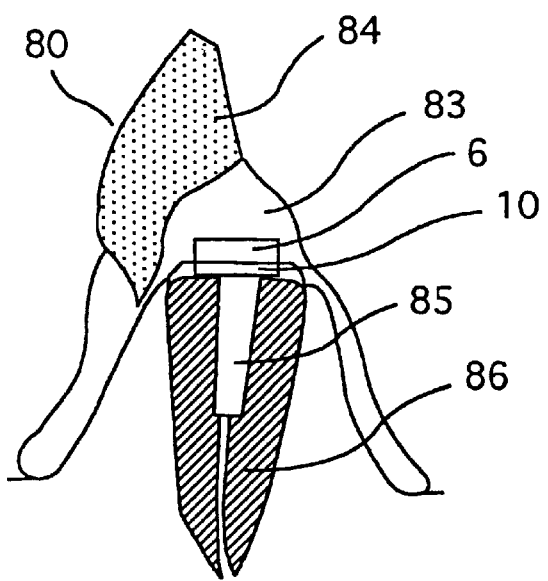
FIG. 8 is a cross section to show how to use the dental magnetic attachment in the denture.
Figure 7:
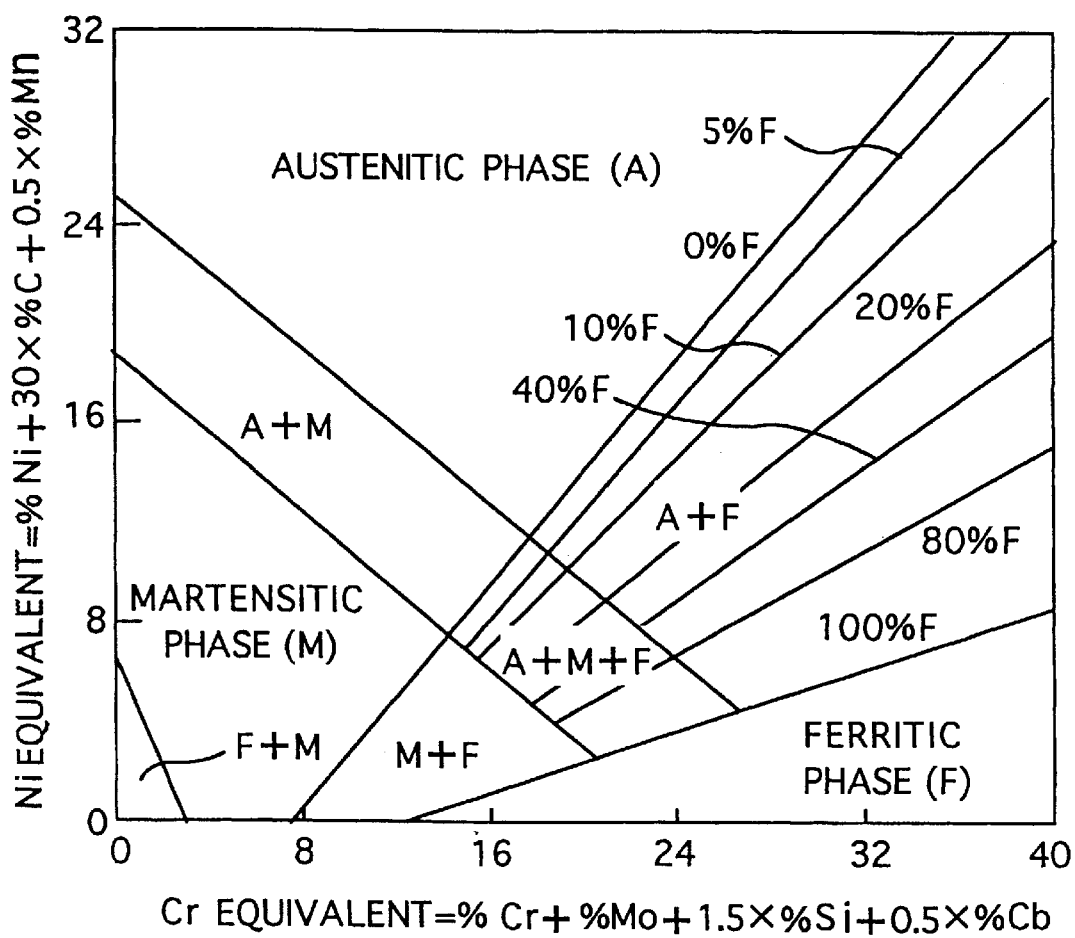
FIG. 7 is a Schaeffler phase diagram to show the phase constitution of the welded part of stainless steel.
Figure 9:
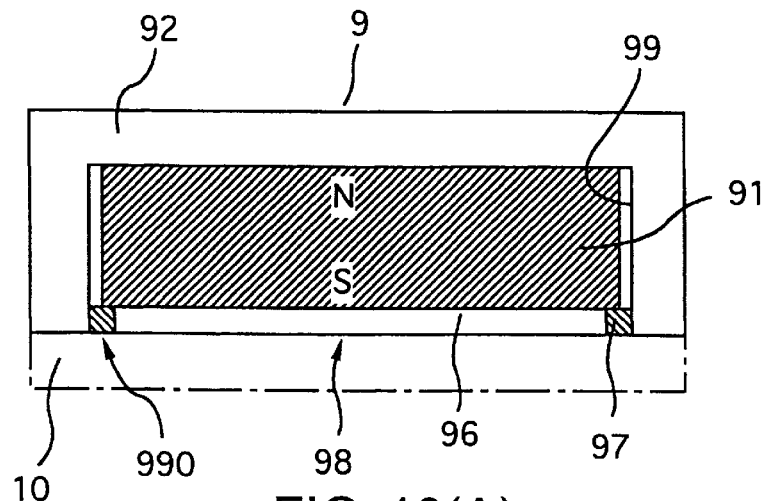
FIG. 9 is a cross section to show the construction of the previous magnetic attachment.
Figure 10A:
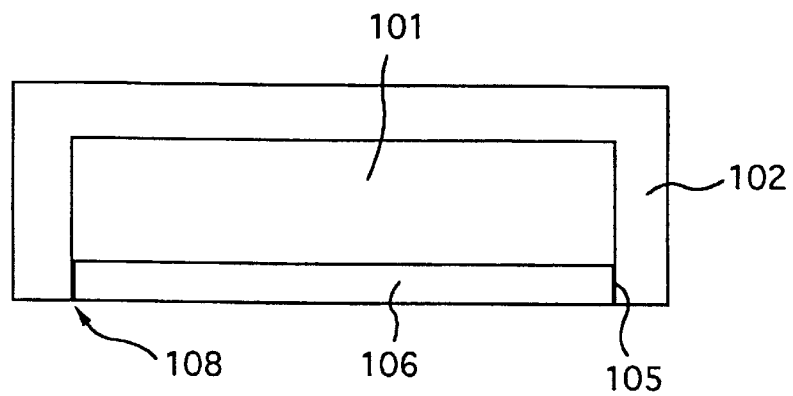
FIGS. 10A and 10B are cross sections showing how to make the nonmagnetic welded part of the previous magnetic attachment.
Figure 10B:
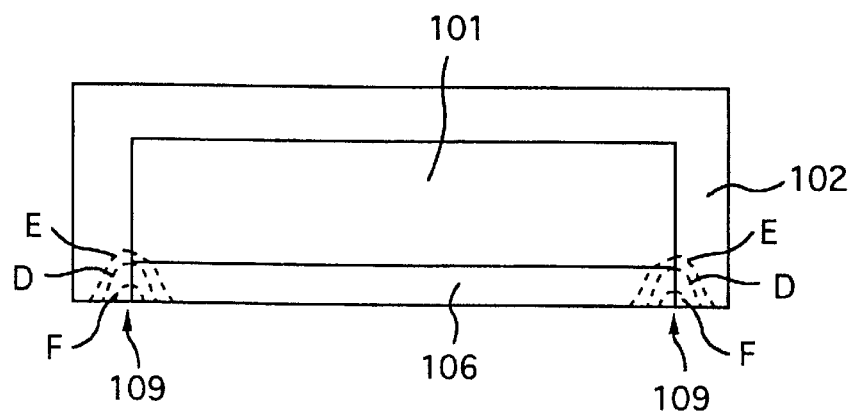

The dental magnetic attachment of the third example as shown in FIG. 3 also is similar to the first one. The different point is that the yoke of the third example has the tapered or round side to hold the magnetic assembly in the denture base 83 of the denture 80 as shown in FIG. 8. The diameter (DK2) of the convex on the side of the yoke is larger than that (DK1) of the bottom of the magnetic assembly.

The above nonmagnetic welded part has austenite phase and chemical composition equal to Cr—Ni type austenitic stainless steel. After the magnet is set into the pit of the cylindrical yoke the sealing disk is welded to the yoke. As seen from FIG. 4(A), there are two parts of the sealing ring 16 made from austenitic stainless steel and Ni coat 17 between the yoke and the sealing disk 15. The yoke, the sealing ring, Ni coat and the sealing disk melt together by laser-welding focusing on the sealing ring to form nonmagnetic welded part. The composition of the welded part is kept around that of austenitic stainless steel used for the non-magnetic sealing ring. Because Ni element in Ni coat enriches Ni content in the welded part, but the welded part of the yoke and the sealing disk supply Cr elements and increases Cr content in it. Both effects on the metallurgical power to change phase constitution is cancelled or balanced.

When the welded part by laser-welding is shallow, a part of the sealing ring made from austenitic stainless steel and Ni coat remain to be not melted.

Figure 6:
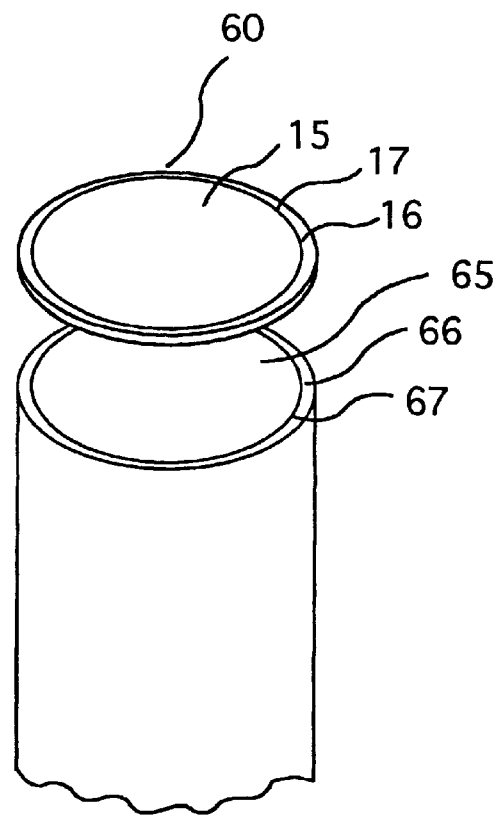
FIG. 6 is an exploded drawing to show how to assemble the sealing plate.

The sealing plate 60 consists of the sealing disk 15, Ni coat 17 and the sealing ring 16. The production method is shown in FIG. 6. A round bar made from soft magnetic stainless steel 65 of 19% Cr-2% Mo-0.2% Ti and remains of iron is Ni coated and then is inserted into a thin tube 66 made from SUS316 type nonmagnetic stainless steel. After that, they are drawn to the designated diameter. At last, they are sliced to thin sealing plates 60.

Next the first example is explained in detail using FIG. 4.

The yoke was made from soft magnetic stainless steel of 19% Cr-2% Mo-0.2% Ti and remains of iron. Its shape was cylindrical with a pit, which looks like a container. As for its dimension, the yoke had the outer diameter of 4.00 mm, the ring thickness of 0.45 mm and height of 1.45 mm. The pit had the diameter of 3.10 mm and the depth of 08.0 mm. The corner of the top side of the yoke was cut around 0.40 mm to show a taper of 45 degree. The bottom corner of the pit of the yoke had a curvature radius of 0.20 mm.

The magnet 41 used was Nd—Fe—B type rare earth magnet having maximum energy product of 42 MGOe. The shape of it was a cylinder to have the diameter of 3.05 mm and the height of 0.6 mm as a well as round corner of a curvature radius of 0.20 mm.

The magnet was inserted in the pit of the yoke 42 and the bottom of the magnet was covered by the sealing plate 60. FIG. 6 shows the structure of the sealing plate 60. It consists of the sealing disk, the Ni coat and the sealing ring. The sealing disk made from 19% Cr-2% Mo-0.2% Ti Soft magnetic stainless steel had the diameters of 2.76 mm, and the Ni coat had a width of 0.01 mm. The sealing ring made from SUS316 type nonmagnetic stainless steel had the diameters of 3.08 mm and the width of 0.25 mm. And the sealing plate was a disk having a thickness of 0.15 mm.

Figure 4A:
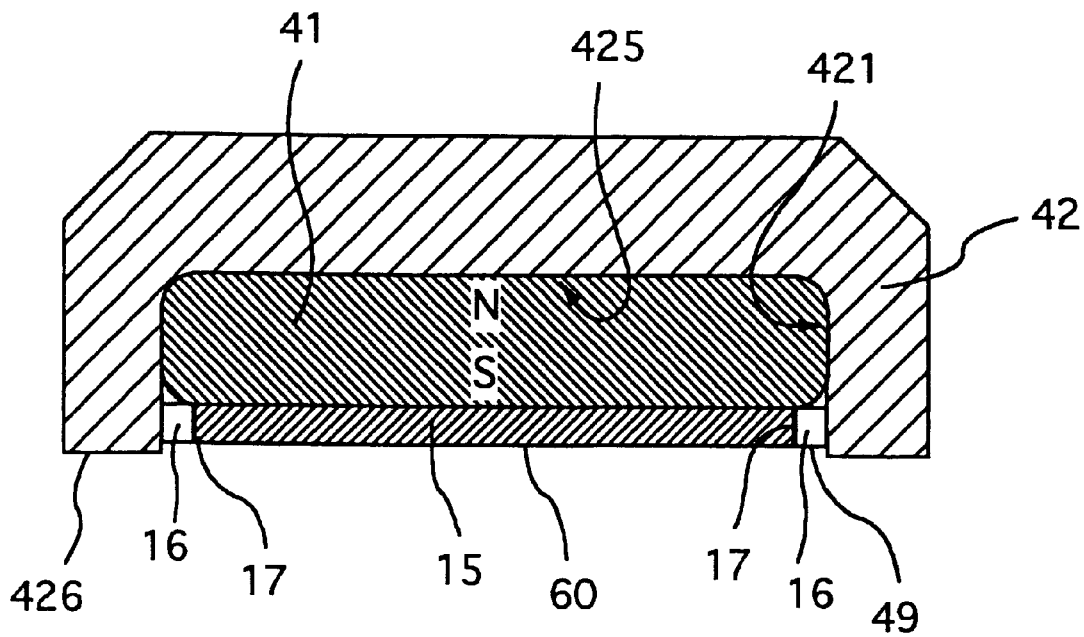
FIGS. 4A and 4B are a cross sections showing how to make the nonmagnetic welded part of the first example.
Figure 4B:
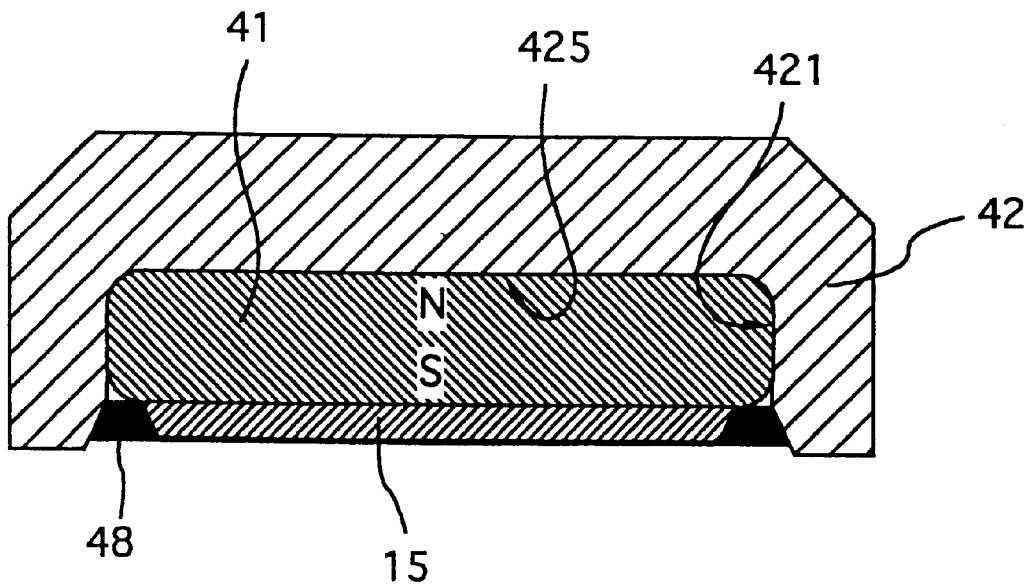

The nonmagnetic welded part as shown in FIG. 4(B) was formed to melt the yoke, the sealing ring, Ni coat and the sealing disk together by laser-welding focusing on the sealing ring to use a laser beam with the diameter of 0.2 mm. The welded part maintained an austenite phase.

There are some problems on welding. One is that a small step which is made in assembling the magnet, the yoke and the sealing plate, remains after welding. Another is that some inequality occurs accompanied by welding.

The step and inequality were removed by polishing or grinding a thickness of about 0.15 mm with a grind dresser of mesh of #500. After polishing, the thickness of the sealing disk decreased about 0.10 mm, the width of the welded part changed from 0.55 mm to 0.35 mm, the diameter of the sealing disk enlarged from 2.40 mm to 2.60 mm and the welded surface became flat. These changes in shape made a remarkable increase in the magnetic attractive force of the dental magnetic attachment.

The magnetic attractive force of the dental magnetic attachment improved from 6.2 N/mm$^2$ to 7.0 N/mm$^2$ by polishing.

The second example as shown in FIG. 2 had a part of the nonmagnetic sealing ring which did not melt by laser-welding with less power than that of the first example after assembling as FIG. 4(a). Here, the laser welding was done using a laser beam with the diameter of 0.2 mm on focusing on the sealing ring or the Ni coat. The part of the nonmagnetic sealing ring not melting was 0.04 mm in thickness. On the other hand the nonmagnetic welded part became about 0.06 mm in thickness after polishing. The sealing plate was about 0.10 mm in thickness and 2.65 mm in diameter. The magnetic attractive force of the second example showed 7.5 N/mm$^2$.

The third example as shown in FIG. 3 had the yoke with the height of 1.45 mm, the outer diameter (DK1) of 4.00 mm and the yoke shell thickness of 0.45 mm. The tapered side of the yoke showed the convex diameter (DK2) of 4.20 mm and the height of 1.30 mm from the bottom surface to the convex line. The pit of the yoke had the diameter of 3.10 mm, the depth of 0.80 mm and a curvature radius of 0.20 mm in the bottom corner. The magnetic attractive force of the third example showed 8.5 N/mm$^2$. The resistance to pull it from the denture resin base, which was estimated by tensile strength in a tensile test, improved 200 N/mm$^2$ from 110 N/mm$^2$ of the first example.

Figure 5:
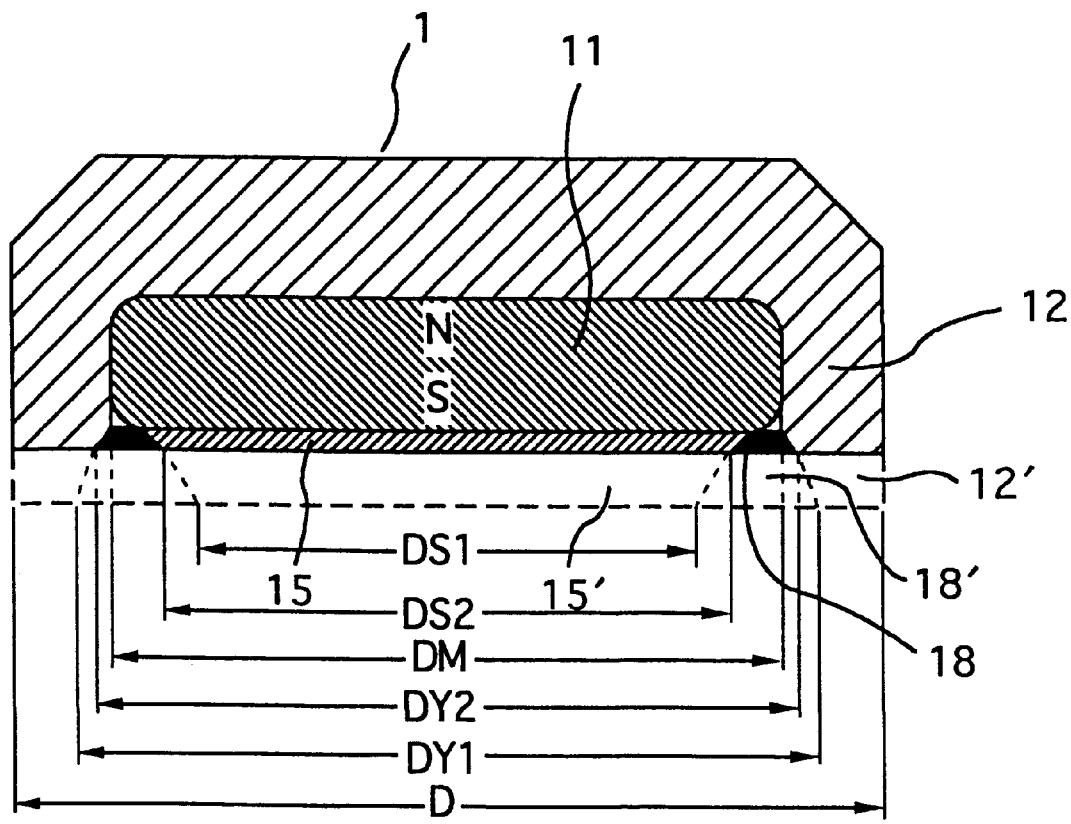
FIG. 5 is a cross section to show the nonmagnetic region and how to polish in the manufacturing process of the first example.

The effect of the present invention is explained using FIG. 5. The first advantage is that the nonmagnetic welded part between the yoke and the sealing disk forms the magnetic isolation to make the magnetic circuit flowing the magnetic flux along the pass from the magnet 11, through the sealing disk 15, the keeper 10, and the yoke 12 finally to the magnet 11 The nonmagnetic welded part can have a part of a nonmagnetic sealing ring not melting. In this case, the magnetic isolation is made more certainly to offer good magnetic attractive force.

The second advantage is that the small width of the welded part improves the magnetic attractive force. The small width of the welded part can be made by means of laser welding on only one welding pass line, which requires the sealing ring of the very small width, and polishing the welded surface.

The third advantage is that the flat surface of the bottom of the attachment makes remarkable improvement in the magnetic attractive force. After welding, there are some inequality and a step on the welded surface. To polish the surface makes it very smooth and flat.

Here, the relationship between polishing the welded surface and the area of the sealing disk is described in detail using FIG. 5. The diameters of the sealing disk before polishing and after polishing are DS2 and DS1 respectively. The diameters of the yoke before polishing and after polishing are DY2 and DY1 respectively. The diameter of the yoke is D and that of the magnet is DM. The sealing disks before polishing and after polishing are T2 and T1 in thickness respectively. The thickness polished out is t.

When the welded surface polished with the thickness of t, the area of the nonmagnetic welded part increases with the area of $((DS2)^2-(DS1)^2)\times 4/\pi$ and the area of the yoke bottom surface increases with the area of $((DY1)^2-(DY2)^2)\times 4/\pi$. These increases in area make a certain improvement in the magnetic attractive force of the dental magnetic attachment.

The present invention offers the dental magnetic attachment which has superior magnetic attractive force with a small nonmagnetic welded part and a flat welded surface to be polished.

What is claimed is:

1. A manufacturing method for a dental magnetic attachment embedded in a denture base which faces to a keeper made of a soft magnetic material and embedded in a root cap for holding a denture in an oral cavity by a magnetic attractive force, said method comprising:

a step for containing a magnet in a pit of a yoke made of a soft magnetic material;

a step for disposing a sealing plate including a circular sealing disk made of a soft magnetic material and an annular austenitic stainless steel part fitted outside of the sealing disk via a nickel layer, at an opening of the pit of the yoke;

a step for forming an annular welded part comprised of an annular non-magnetic welded part by heating and melting the sealing disk, the austenitic stainless steel part, the nickel layer and the yoke with a laser beam focused on the austenitic stainless steel part and the nickel layer; and a step for polishing a surface of the yoke, the sealing plate and the welded part so that the non-magnetic welded part is left.

2. The manufacturing method according to claim 1, wherein the surface of the yoke, the sealing plate and the welded part are polished until a height of the non-magnetic welded part becomes equal to a half of a thickness of the sealing disk.

3. The manufacturing method according to claim 2, wherein the surface of the yoke member, the sealing plate and the welded part are polished at least 0.5 mm in a thickness direction thereof, and the sealing disk has a thickness of 0.05 to 0.15 mm.

* * * * *